United States Patent [19]

Lynch et al.

[11] Patent Number: 4,855,128
[45] Date of Patent: Aug. 8, 1989

[54] SACCHARIDE INHIBITION OF DENTAL PLAQUE

[75] Inventors: Donald M. Lynch, Flemington; Benjamin Appelbaum, Flanders, both of N.J.

[73] Assignee: Warner-Lambert Company, Morris Plains, N.J.

[21] Appl. No.: 143,992

[22] Filed: Jan. 14, 1988

[51] Int. Cl.$^4$ .............................................. A61K 7/16
[52] U.S. Cl. ...................................................... 424/49
[58] Field of Search ...................................... 424/49–58

[56] References Cited

U.S. PATENT DOCUMENTS

| | | | |
|---|---|---|---|
| 4,051,234 | 9/1977 | Gieske et al. | 424/52 |
| 4,627,972 | 12/1986 | Gioffre et al. | 424/49 |
| 4,645,662 | 2/1987 | Nakashima et al. | 424/49 |
| 4,689,216 | 8/1987 | Greene | 424/49 |
| 4,775,525 | 10/1988 | Pera | 424/54 |

OTHER PUBLICATIONS

Kaosoap, C.A. 79, #70244n (1973).
Muehlemann et al, C.A. 95, #30423u (1981).
Becker, C.A. 96, #57601h (1982).
Naganuma, C.A. 107, #16282g (1987).
Miyahara, C.A. 107, #242468d (1987).
Rolla, C.A. 108, #81860d (1988).
Ibsen, C.A. 108, #226687q (1988).

*Primary Examiner*—Shep K. Rose
*Attorney, Agent, or Firm*—Gary M. Nath; Charles A. Gaglia, Jr.

[57] ABSTRACT

The invention provides plaque-inhibitory agents useful in oral compositions such as mouthwashes, toothpastes, mouthrinses, dental creams, toothpowders etc. comprising polysaccharides such as xanthan gum, gum tragacanth (pectin), guar gum, gum karaya, chondroitin sulfate, polygalacturonic acid, sodium alginate and carrageenans of the kappa/lambda configuration. The agents are effective in plaque-inhibiting at concentrations between about 0.0025% and 2.000% on a weight/volume basis.

15 Claims, No Drawings

SACCHARIDE INHIBITION OF DENTAL PLAQUE

BACKGROUND OF THE INVENTION

This invention is concerned with a method of inhibiting the formation of dental plaque which employs certain saccharides and oral compositions containing such saccharides.

Dental plaque is a dense, heterogeneous, non-calcified bacterial mass which firmly adheres to the tooth surface to the degree that it resists wash off by salivary flow. The bacteria contained in plaque possess varying degrees of pathogenic activity and are responsible in part for dental caries, gingivitis, mouth odor and periodontal disease. Streptococcus mutans is one of the bacteria found in dental plaque and it has been found to possess a high cariogenic potential in a variety of laboratory animals. Actinomyces viscosus, another dental plaque bacteria, has been associated with gingivitis and root surface caries. Obviously the removal or inhibition of plaque formation would significantly reduce the occurences of these diseases.

Plaque is generally removed by employing mechanical cleaning, using an abrasive dentifrice, by flossing or by rinsing with an antibacterial (anti-plaque) mouthrinse. However, plaque deposited between teeth is difficult to remove by mechanical cleaning and flossing does not remove plaque located at the gingival margin. Anti-plaque mouthrinses serve as an adjunct to mechanical plaque removal. To date, an anti-plaque mouthrinse that can take the place of mechanical plaque removal has not been discovered.

Plaque formation on a clean tooth, it is generally believed, starts with the formation of a pellicle or cuticle composed of salivary constituents. The pellicle is an amorphous, membranous layer which covers the enamel surface and is considered to consist of salivary glycoproteins, polypeptides and other salivary constituents which have become selectively adsorbed on the tooth surface. The pellicle is usually free of bacteria. The pellicle is formed within minutes after the tooth is cleaned and the adsorbed materials eventually become transformed into a highly insoluble coating. Thereafter an initial adherence of specific bacteria occurs on the acquired pellicle. These bacteria produce extracellular polysaccharides (called glucans) from sucrose catalyzed by the enzyme glucosyl transferase which aid entrapment and adherence of other bacteria.

The cariogenic potential of S. mutans for example is associated with its ability to form dental plaque and this ability is dependent upon the synthesis of extracellular polysaccharides from sucrose. In addition to initial adherence, the coaggregation of various species of bacteria occurs in which specific bacteria attach to each other by synthesizing polymers which bind similar and dissimilar cells together although there are some species that will not coaggregate.

In an effort to rid teeth of plaque the prior art has described agents incorporated into oral preparations such as dentifrices which inhibit the formation of plaque rather than its removal as described above.

In U.S. Pat. No. 4,117,107 for example, a method for retarding pellicle and plaque formation is described which includes contacting sites of plaque formation and growth with a dental preparation containing certain fatty acid amido betaines.

Similarly, U.S. Pat. No. 4,130,637 provides betaine compounds derived from higher alkyl dimethyl carboxylic acid quarternary ammonium compounds effective in controlling dental plaque without producing an esthetically unacceptable discoloration of the teeth.

U.S. Pat. No. 4,360,515 provides compounds for the prevention of attachment of dental plaque to the teeth comprising certain sulfonated alkoxynaphthalenes and the pharmaceutically acceptable salts thereof.

U.S. Pat. No. 4,619,825 describes a plaque-inhibiting composition comprising an aqueous dispersion of emulsan which can be incorporated in dental preparation toothpastes or mouthwashes.

The present invention, on the other hand, provides an effective plaque inhibiting composition containing certain saccharides which act to prevent the coaggregation of bacteria in the formation of plaque and therefor substantially inhibit its complex formation. The saccharides are non-toxic, suitable for oral application in most oral compositions and are effective at low concentrations.

SUMMARY OF THE INVENTION

In brief, the invention comprises an oral composition containing certain agents which inhibit the coaggregation of bacteria and thereby inhibit its complete formation.

The saccharides comprise polysaccharides such as xanthan gum, gum tragacanth, pectin, guar gum, gum karaya, chondroitin sulfate, polygalacturonic acid, sodium alginate and carrageenans of the kappa/lambda configuration. These agents can be used in aqueous-based oral compositions at concentrations of between about 0.0025% and 2.000% on a weight/volume basis to be effective in inhibiting coaggregation.

DETAILED DESCRIPTION OF THE PREFERRED EMBODIMENTS

The plaque inhibitory agents of the present invention include certain naturally-occuring saccharides which inhibit the interaction of oral microorganisms or bacteria to substantially prevent coaggregation thereby reducing or eliminating the build up of plaque. These saccharides comprise polysaccharides such as xanthan gum, gum tragacanth, pectin, guar gum, gum karaya, chondroitin sulfate, polygalacturonic acid, sodium alginate and carrageenans of the kappa/lambda configuration. Many of the polysaccharides useful herein such as xanthan gum and gum tragacanth have previously found application as inert ingredients in formulations containing pharmaceutically active agents as for example binders, stabilizers or thickeners. However, these saccharides are not known to possess any biological or pharmaceutical activity in and of themselves. Other agents described in this invention such as chondroitin sulfate is used as antihyperlipoproteinemic or wound healing preparations. None of the saccharides have been described heretofore as anti-plaque agents.

The agents can be incorporated in any aqueous-based oral composition such as a mouthwash, toothpaste and the like and will effectively inhibit plaque formation at concentrations which are far less than their normal use levels in other compositions. Generally they can be used at concentrations of between about 0.0025% and 2.000% and preferably between about 0.05% and 1.0% (weight/volume basis) to inhibit coaggregation. For example, guar gum and xanthan gum which are normally used in foods at levels up to an often greater than 3% to 4% on a weight/volume basis show anti-plaque activity in aqueous media at levels between 0.15% and 0.07% on the same basis.

An Assay was developed to determine the inhibition of coaggregation of *Streptococcus sanguis* and *Actinomyces viscosus,* two organisms commonly found in plaque. Polygalacturonic acid was found to inhibit at low concentrations (approximately 2mM). Xanthan gum, guar gum and gum tragacanth are also extremely effective, effecting 50% inhibition of coaggregation at concentrations of 0.05%, 0.15% and 0.35%, respectively. Gum Tragacanth contains mostly galacturonic acid.

Pectin, chondroitin sulfate and sodium alginate demonstrate substantial inhibition according to the assay. Carrageenans of the kappa and lambda configuration show moderately effective inhibition but carrageenans of the iota configuration exhibit poor inhibitory characteristics.

The anti-plaque agents of the invention can be readily incorporated into aqueous or aqueous/alcohol-based oral compositions such as a mouthwash, spray, rinse, toothpaste, dental cream, gel or toothpowder.

The agents should be present in amounts of from about .0025% to about 4% by weight of the total weight of the composition. Preferably the complex is present in amounts from about .01% to about 2% by weight of the total weight and most preferably from about .05% to about 1.0%.

In one form of the invention, the oral composition may be a liquid such as a mouthwash, spray or rinse. In such a composition the vehicle is typically a water/alcohol mixture. Generally the ratio of total water to alcohol is in the range of from about 1:1 to about 20:1, preferably about 3:1 to about 20:1 and most preferably about 3:1 to about 10:1 by weight. The total amount of water/alcohol mixture in a mouthwash preparation is typically in the range from about 45% to about 82.5% by weight of the composition. The pH value of such mouthwash preparation is generally from about 4 to about 9 and preferably from about 5 to about 8.5. A pH below 4 is irritating to the oral cavity and a pH greater than 9 results in an unpleasant mouth feel.

Fluorine providing compounds may be present in the oral preparations of this invention. These compounds may be slightly water-soluble or may be fully water-soluble and are characterized by their ability to release fluoride ions or fluoride containing ions in water. Typical fluorine providing compounds are inorganic fluoride salts such as soluble alkali metal, alkaline earth metal, and heavy metal salts, for example, sodium fluoride, potassium fluoride, ammonium fluoride, cuprous fluoride, zinc fluoride, stannic fluoride, stannous fluoride, barium fluoride, sodium fluorosilicate, ammonium fluorosilicate, sodium fluorozirconate, sodium monofluorophosphate, aluminum mono- and difluorophosphate and fluorinated sodium calcium pyrophosphate.

Alkali metal, tin fluoride and monofluorophosphates such as sodium and stannous fluoride, sodium monofluorophosphate and mixtures thereof are preferred.

In an oral liquid composition such as a mouthwash, the fluorine providing compound is generally present in an amount sufficient to release up to about 0.15%, preferably about 0.001% to about 0.1% and most preferably from about 0.001% to about 0.05% fluoride by weight of the preparation.

The oral composition may also contain additional flavorants and colorants.

In the instance where auxiliary sweeteners are utilized, the present invention contemplates the inclusion of those sweeteners well known in the art, including both natural and artificial sweeteners. Thus, additional sweeteners may be chosen in minor amounts from the following non-limiting list.

A. Water-soluble sweetening agents such as monosaccharides, disaccharides and polysaccharides such as xylose, ribose, glucose, mannose, galactose, fructose, dextrose, sucrose, maltose, partially hydrolyzed starch or corn syrup solids and sugar alcohols such as sorbitol xylitol, mannitol and mixtures thereof.

B. Water-soluble artificial sweeteners such as the soluble cyclamate salts and the like.

C. Dipeptide based sweeteners such as L-phenylalanine methyl ester and materials described in U.S. Pat. No. 3,492,131 and the like.

In general, the amount of sweetener will vary with the desired amount of sweeteners selected for a particular oral preparation. This amount will normally be 0.01% to about 40% by weight. The water-soluble sweeteners described in category A above, are preferably used in amounts of about 5% to about 40% by weight, and most preferably from about 10% to about 20% by weight of the final composition. In contrast, the artificial sweeteners described in categories B and C are used in amounts of about 0.005% to about 5.0% and most preferably about 0.05% to about 2.5% by weight of the final composition. These amounts are ordinarily necessary to achieve a desired level of sweetness independent from the flavor level achieved from flavorants.

Suitable flavorings include both natural and artificial flavors, and mints such as peppermint and spearmint. Citrus flavors such as orange and lemon, various fruit flavors, both individual and mixed, and the like are contemplated. The flavorings are generally utilized in amounts that will vary depending upon the individual flavor, and may, for example, range in amounts of about 0.05% to about 6% by weight of the final composition.

The colorants useful in the present invention include the pigments which may be incorporated in amounts of up to about 2% by weight of the composition. Also, the colorants may include other dyes suitable for food, drug and cosmetic applications, known as FD & C and D & C dyes. The materials acceptable for the foregoing spectrum of use are preferably water-soluble. Illustrative examples include the yellow dye, known as D & C Yellow #10, and the dye known as FD & C Green #3 which comprises a triphenylmethane dye. A full recitation of all FD & C and D & C colorants useful in the present invention and their corresponding chemical structures may be found in the Kirk-Othmer Encyclopedia of Chemical Technology, 3rd Edition, in Volume 6, at pages 561–595, which text is accordingly incorporated herein by reference.

The oral compositions may also be substantially solid or pasty in character such as a dental cream, toothpaste or a toothpowder. Solid or pasty oral preparations contain polishing materials. Typical polishing materials are abrasive particulate materials having particle sizes of up to about 20 microns. Nonlimiting illustrative examples include: water-insoluble sodium metaphosphate, potassium metaphosphate, tricalcium phosphate, dihydrated calcium phosphate, calcium pyrophosphate, magnesium orthophosphate, trimagnesium phosphate, calcium carbonate, alumina, aluminum silicate, zirconium silicates, silica, bentonite, and mixtures thereof. Polishing materials are generally present in an amount from about 20% to about 82% by weight of the oral preparation. Preferably, they are present in amounts from about 20% to about 75% in toothpaste, and from about 70% to about 82% in toothpowder. For toothpaste and dental creams the water content is about 25% to 50% by weight.

In clear gels, a polishing agent of colloidal silica and alkali metal aluminosilicate complexes are preferred since they have refractive indicies close to the refractive indicies of gelling agent liquid systems commonly used in dentifrices.

In general, the anti-plaque oral compositions of the present invention are prepared as follows. The sweetener is dissolved in water to form a solution. The anti-plaque agent is added to the solution and mixed until dissolved. Then sufficient water alcohol or mixtures thereof are added with mixing until the final solution volume is reached. When colorants, additional sweeteners and similar additives are included in the composition, they are added at the same time the sweetener is added. The anti-plaque agent may also be added as the final ingredient.

In order to more fully describe the present invention, the following non-limiting Examples are submitted.

EXAMPLE 1

This Example describes an assay for determining the inhibition of coaggregation by various agents according to the invention and the results obtained thereby.

A. Preparation of Growth Medium:

*Streptococcus sanguis* strain 34 (originally derived from human dental plaque), and *Actinomyces viscosus* T14V were grown in a medium containing the dialyzable portion of Trypticase and Yeast Extract, supplemented with salts and a carbon source, as follows: A concentrated stock solution (20×, to make 10 liters of growth medium) containing Trypticase Peptone (BBL, 170 grams) and Yeast Extract (40 grams) as prepared in a liter of distilled water. This solution was subsequently ultrafiltered in an Amicon model DC-2 hollow fiber ultrafiltration cell, using an H1P10–20 hollow fiber cartridge (molecular weight cut off of 10,000 daltons), and the filtrate (that material of <10,000 daltons molecular weight) saved. The material was concentrated to a final volume of approximately 100 ml, and then reconstituted to one liter, after which the procedure was repeated for a total of three cycles, saving the filtrates at each step. The filtrates were collected into a vessel chilled on ice, combined, and the total volume measured. This stock solution was distributed in aliquots sufficient to make one liter of medium, and stored at $-20°$ C. until used.

To prepare the growth medium, the appropriate volume of the 10× stock Trypticase-Yeast Extract stock solution was thawed, and to it added (in grams per liter): NaCl, 5, and $K_2HPO_4$, 2.5, and the volume adjusted to 1 liter with distilled water. The medium was sterilized by autoclaving. Where indicated, glucose was added as a carbon source to give a final concentration of 0.2%. Initially, this was done by aseptically adding filter-sterilized glucose solutions to the autoclaved medium. For later experiments, glucose was added to the growth medium prior to sterilization.

B. Growth Conditions:

Streptococci were grown in medium containing 0.2% glucose. Starter cultures were prepared by inoculation from a frozen stock culture, and incubated overnight at 37° C. under aerobic (not anaerobic) conditions. This starter culture was used as a 0.5–1.0% inoculum to inoculate larger quantities of medium (100 ml-1 liter), which were subsequently incubated for 16 hours at 37° C. Growth conditions were similar for the actinomycete, except that they were grown under an anaerobic environment (10% hydrogen-5% carbon dioxide, and 85% nitrogen). The starter culture was incubated for 24–48 hours, but the larger cultures required 48 hours incubation.

C. Preparation of Cells for Coaggregation Assays:

After growth, the cells were collected by centrifugation (10,000 × g, 15 minutes, 4° C.) and washed three times in PBS (phosphate-buffered saline, 0.025 M, pH 8.0 containing 1.46g NaCl per liter). The cells were then suspended in PBS such that when the stock cell suspension was diluted 1:10, it would produce an Absorbance at 660 nm of between 0.22–0.24, equivalent to an initial Absorbance of 2.2–2.4. The cells were stored on ice for use during the day, but warmed to ambient temperature before initiation of coaggregation. Residual cells were stored for further use by resuspension in a solution of 50% glycerol in water, and stored at 4° C. On the day of use, the cells were then collected by centrifugation, washed twice with PBS, and the trubidity adjusted as described above. It has been found that cells could be stored for at least 2 months under these conditions with no significant loss of coaggreating activity.

D. Coaggregation Assay:

Assays were performed in a final volume of 1.0 ml in 190×75 mm disposable culture tubes, in duplicate. Controls consisted of 0.8 ml of either cell suspension, and 0.2 ml PBS. The coaggregating mixtures contained 0.4 ml of each cell suspension, and PBS to make 1.0 ml. Inhibitors were added from stock solutions to give the desired final concentrations, and, where necessary, the salt concentrations adjusted using a double-strength (2X) PBS solution. The mixtures were mixed on a Vortex mixer for 10 seconds at a speed setting of 6, incubated at ambient temperature for 10 minutes, vortexed again, and allowed to stand for 2 hours. After the 2 hours, the mixtures were again vortexed, and scored visually and quantitatively.

1. The scale for visual scoring of coaggregation is:

Score: Criteria:

Zero No visible aggregates in the cell suspension.

Plus 1 Small uniform aggregates in suspension.

Plus 2 Definite coaggregates easily seen but suspension remained turbid without immediate settling of coaggregates.

Plus 3 Large coaggregates which settled rapidly, leaving some turbidity in the supernatant fluids.

Plus 4 Clear supernatant fluid and large coaggregates which settled immediately.

2. To quantitate coaggregation, tubes containing the reaction mixtures were centrifuged in an IEC Clinical Centrifuge (using an IEC #215 rotor with IEC #369 multiple tube carriers). After a 1 minute centrifugation (ambient temperature, speed setting of 2), the supernatant fluids were withdrawn, and their Absorbance at 660 nm ($A_{660}$) determined using a spectrophotometer. These centrifugation conditions enabled the separation of the coaggregates from the free cells remaining in the mixture. Coaggregation was then quantitated using the following formula:

A. Percent coaggregation $$\frac{\frac{A_{660}\ T14V^* + A_{660}\ SS^{}}{2} - (A_{660}\ \text{Experimental}^{*})}{\frac{A_{660}\ T14V + A_{660}\ SS}{2}} \times 100\%$$

*T14V Actinomyces viscosus strain T14V, or other actinomycete.
**SS. Streptococcus sanguis 34, or other streptococcal strain.
***Experimental: Coaggregating mixtures.

The percent coaggregation in the presence of an inhibitor is normalized to that of the control, and percent inhibition is 100% minus the percent coaggregation in the presence of inhibitor.

The data is plotted semi-logarithmically, and the concentration of a given agent that is able to effect 50% inhibition of coaggregation is then determined from the graph. The data reported represents the average from two independent experiments, each run in duplicate.

EXAMPLES 2 & 3

The agents of the present invention were tested for coaggregation inhibition using the assay described in Example 1 along with other candidate inhibitors. In a first test, Example 2, the effect of certain carbohydrates on the A. viscosus T14V-S. sanguis 34 coaggregation was determined including glucuronic acid and polygalacturonic acid. The results are summarized in Table 1 below.

TABLE 1

| Agent | Coaggregation to effect 50% Inhibition |
|---|---|
| Lactose | 3.6 mM (n=13)$^a$ |
| Galactose | 22 mM (n=6)$^a$ |
| Galactoseamine | 35 mM |
| 2-deoxy-D-galactose | 20 mM |
| D-Fructose (6-deoxy-D-galactose) | 20 mM |
| Lactobionic acid | 3-4 mM, then rebounds |
| Lactulose | 35 mM |
| Glucuronic acid | 15 mM, then rebounds |
| Polygalacturonic acid | 0.1% (approx. 2 mM)$^b$ |
| Glucose | >100 mM |
| Maltose | >100 mM |
| Mannose | >100 mM |
| Sucrose | >100 mM |
| Trehalose | >100 mM |

$^a$n indicates number of experiments
$^b$Calculated on a molecular weight estimated by the supplier to be between 4000–6000 daltons.

As Table 1 shows, lactobionic acid (4-[beta-D-galactosido]-D-gluconic acid) inhibits coaggregation at very low concentrations (3-4 mM), similar to that observed with lactose, a known plaque inhibitor. It was also noted that lactobionic acid also promotes a rebound effect as its concentration is increased up to 100 mM, resulting in 10% inhibition at the higher concentration. A similar rebounding effect was also observed with glucuronic acid which showed significant coaggregation inhibition (15 mM). Polygalacturonic acid (molecular weight estimated at between 4000–6000) effected 50% inhibition at 0.1% (approximately 2 mM).

In a second test, Example 3, a number of watersoluble gums and polysaccharides were examined by the assay of Example 1 for their ability to inhibit coaggregation of A. viscosus T14V-S. sanguis 34 including xanthan gum, guar gum, gum tragacanth, pectin, gum karaya, chondroitin sulfate and certain carrageenans. Gum tragacanth contains mostly galacturonic acid. The results are summarized in Table 2 below.

TABLE 2

| Agent | Concentration to effect 50% Inhibition |
|---|---|
| Xanthan gum | 0.05% |
| Guar gum | 0.15% |
| Gum tragacanth | 0.35% |
| Pectin | 0.8% |
| Chondroitin sulfate | 4% |
| Gum karaya | 17% inhibition at 0.5% |
| Carrageenans | |
| Sigma C1013 | Average of 20% inhibition at 0.5% |
| (Kappa/lambda 80:20 | |
| Sigma C1138 | 6% inhibition at 0.5% |
| (Iota) | |
| FMC Lambda carrageenans: | |
| Viscarin GP209 | >0.2%$^b$ |
| Viscarin SD389 | >0.2%$^b$ |
| Agar | >0.2%$^c$ |
| Agarose | >0.2%$^c$ |
| Sodium alginate | 32% inhibition at 0.5% |
| Soluble starch | 8% inhibition at 1.0% |

$^a$Results represent average data from two independent experiments.
$^b$Highest concentration tested was 0.5% carrageenan, but this resulted in a solution which was too thick to score for coaggregation by either method.
$^c$Concentrations as high as 0.1% were tested, but the mixture solidified upon cooling, and coaggregation could not be determined.

As Table 2 shows, xanthan and guar gums, and gum tragacanth were the most effective of the tested wherein concentrations of 0.05%, 0.15%, and 0.35% respectively effected 50% inhibition of coaggregation. Pectin and chondroitin sulfate effected almost 50% inhibition at 0.8% and 4%, respectively. Agar and agarose did not demonstrate inhibition. The inhibition by sodium alginate was substantial. Soluble starch and iota carrageenans demonstrated poor inhibition. The lambda carrageenans did not exhibit inhibition but the kappa/lambda carrageenans demonstrated significant inhibition.

We claim:

1. An oral aqueous or aqueous/alcoholic-based antiplaque mouthwash, mouthspray, or mouthrinse composition for inhibiting plaque comprising an antiplaque agent, said antiplaque agent consisting essentially of an effective amount of from at least about .0025% w/v. to not more than about 4% w/v a polysaccharide selected from the group consisting of xanthan gum, gum tragacanth, guar gum, gum karaya, chondroitin sulfate, polygalacturonic acid, and carrageenans of the kappa/lambda configuration.

2. The oral composition of claim 1 which comprises a mouthwash.

3. The oral composition of claim 1 which comprises a mouthrinse.

4. The oral composition of claim 1 wherein said composition is an aqueous medium and said effective amount is from 0.0025% to 4.000% by weight of the total weight of said composition.

5. The oral composition of claim 4 wherein said aqueous medium is an alcohol/water mixture.

6. The oral composition of claim 5 wherein the ratio of water to alcohol is from about 1:1 to about 20:1.

7. The oral composition of claim 1 which further comprises a fluorine-providing compound.

8. The oral composition of claim 1 which further comprises a flavorant.

9. The oral composition of claim 1 which further comprises a colorant.

10. The oral composition of claim 1 which further comprises a natural or artificial sweetener.

11. A method for inhibiting the formation of plaque comprising contacting dentin with the oral composition of claim 1.

12. A method for inhibiting the formation of plaque comprising contacting dentin with the oral composition of claim 2.

13. A method for inhibiting the formation of plaque comprising contacting dentin with the oral composition of claim 4.

14. The oral composition of claim 1 wherein said polysaccharide is present in an amount of from .0025% to 2% by weight of the total weight of the composition.

15. The oral composition of claim 1 wherein said polysaccharide is present in an amount of from 0.05% to 1% by weight of the total weight of said composition.

* * * * *